United States Patent
Abhyankar et al.

(10) Patent No.: US 10,766,854 B2
(45) Date of Patent: Sep. 8, 2020

(54) SYNTHESIS METHOD FOR THE PREPARATION OF DIBENZOATE COMPOUNDS, SUCH AS 4-[BENZOYL(METHYL)AMINO]PENTANE-2-YL DIBENZOATE

(71) Applicant: SABIC GLOBAL TECHNOLOGIES B.V., Bergen op Zoom (NL)

(72) Inventors: Shirish Shrikant Abhyankar, Bangalore (IN); Abbas-Alli Ghudubhai Shaikh, Bangalore (IN); Sivalingam Gunasekaran, Bangalore (IN); Jaiprakash Brijlal Sainani, Bangalore (IN)

(73) Assignee: SABIC GLOBAL TECHNOLOGIES B.V., Bergen op Zoom (NL)

(*) Notice: Subject to any disclaimer, the term of this patent is extended or adjusted under 35 U.S.C. 154(b) by 0 days.

(21) Appl. No.: 16/756,577

(22) PCT Filed: Oct. 19, 2018

(86) PCT No.: PCT/EP2018/078701
§ 371 (c)(1),
(2) Date: Apr. 16, 2020

(87) PCT Pub. No.: WO2019/077104
PCT Pub. Date: Apr. 25, 2019

(65) Prior Publication Data
US 2020/0239407 A1 Jul. 30, 2020

(30) Foreign Application Priority Data
Oct. 20, 2017 (EP) .................................. 17197589

(51) Int. Cl.
C07C 231/14 (2006.01)
(52) U.S. Cl.
CPC ................... *C07C 231/14* (2013.01)
(58) Field of Classification Search
CPC .... C07C 231/14; C07C 231/02; C07C 233/69
See application file for complete search history.

(56) References Cited

U.S. PATENT DOCUMENTS

2015/0259448 A1* 9/2015 Taftaf .................. C07C 233/18
526/124.6

OTHER PUBLICATIONS

International Search Report for International Application No. PCT/EP2018/078701, filed Oct. 19, 2018, dated Jan. 28, 2019, 4 pages.
Written Opinion for International Application No. PCT/EP2018/078701, filed Oct. 19, 2018, dated Jan. 28, 2019, 3 pages.

* cited by examiner

*Primary Examiner* — Jafar F Parsa
*Assistant Examiner* — Blaine G Doletski
(74) *Attorney, Agent, or Firm* — Cantor Colburn LLP

(57) ABSTRACT

The present invention relates to a process for synthesis of a compound according to Formula (A): wherein $R_1$ is a substituted or unsubstituted aryl having 6 to 20 carbon atoms; preferably substituted or unsubstituted phenyl; $R_2$ is a straight or branched alkyl having 1 to 12 carbon atoms; and $R_3$ is a straight or branched alkyl having 1 to 12 carbon atoms; starting from a di-keto compound according to Formula (B) wherein $R_3$ is as shown above, which compound is converted into a ketoenamine compound according to Formula (C) wherein $R_2$ and $R_3$ are as shown above, which ketoenamine compound is then reduced to an amino alcohol according to Formula (D), wherein $R_2$ and $R_3$ are as shown above, that is subsequently converted into a compound according to Formula (A): characterized in that the ketoenamine is reduced into an amino alcohol using a nickel aluminium alloy in an aqueous solution of an inorganic base.

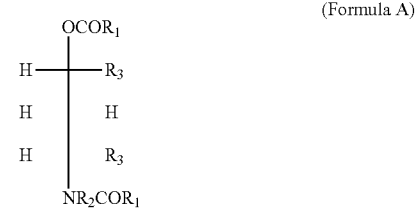

(Formula A)

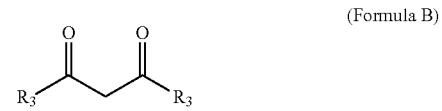

(Formula B)

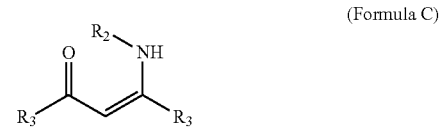

(Formula C)

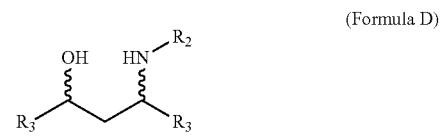

(Formula D)

13 Claims, No Drawings

SYNTHESIS METHOD FOR THE PREPARATION OF DIBENZOATE COMPOUNDS, SUCH AS 4-[BENZOYL(METHYL)AMINO]PENTANE-2-YL DIBENZOATE

CROSS REFERENCE TO RELATED APPLICATIONS

This application is a National Stage application of PCT/EP2018/078701, filed Oct. 19, 2018, which claims the benefit of European Application No. 17197589.9, filed Oct. 20, 2017, both of which are incorporated by reference in their entirety herein.

BACKGROUND

Internal electron donors are one of the components of Ziegler Natta catalysts for the polymerization of propylene. One of these known donors is called AB (or 4-[benzoyl(methyl)amino]pentane-2-yl benzoate or 4-(methylamino)-pentan-2-ol dibenzoate), a so-called non-phthalate internal donor of the benzoate type. A synthesis of AB is disclosed in EP 2 867 264 B1 and consists of the following three steps: step 1) the formation of a ketoenamine from acetyl acetone; step 2) the reduction of said ketoenamine to an amino alcohol using sodium metal (Na) in an isopropanol-tetrahydrofuran solvent mixture; and step 3) the benzoylation of the amino alcohol to AB using a benzoyl chloride as reagent and pyridine as a base and methylene dichloride as a solvent. After steps 1) and 2) the intermediate products are isolated and purified for use in the next step, being steps 2) and 3) respectively. The overall yield of this known process is approximately 54%.

It is an object of the present invention to propose an improved and alternate process for the synthesis of dibenzoate compounds, such as 4-(methylamino) pentan-2-ol dibenzoate (AB donor). It is an object of the present invention to develop an economical process for the production of dibenzoate compounds, such as AB donor, that can be used on large scale without the use of pyrophoric reagents.

SUMMARY

One or more objects are obtained with the process according to the present invention. The following formulas are used in the present description.

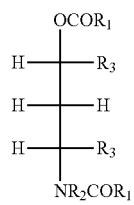

(Formula A)

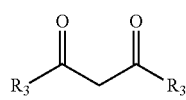

(Formula B)

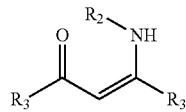

(Formula C)

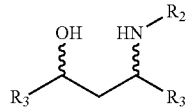

(Formula D)

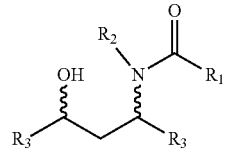

(Formula E)

The compound according to Formula A is a so-called carbonate-carbamate compound, having a carbonate moiety (—O—C(=O)) linked to a carbamate moiety (—N(R)—C(=O)—). Formula B is a di-keto compound. In case that both $R_3$ groups are methyl, this compound is called acetyl acetone, also called 2,4-pentane di-one. Formula C is a ketoenamine compound. In case that $R_3$ and $R_2$ are all methyl groups, this compound is 4-(methylamino) pent-3-en-2-one. Formula D is an amino alcohol. In case that $R_3$ and $R_2$ are all methyl groups, this compound is 4-(methylamino)-pentan-2-ol. Formula E is a monobenzoate. In case that $R_3$ and $R_2$ are all methyl groups, and $R_1$ is phenyl this is N-(4-hydroxypentan-2-yl)-N-methylbenzamide.

The present invention provides for a process for synthesis of a compound according to Formula A; wherein $R_1$ is a substituted or unsubstituted aryl having 6 to 20 carbon atoms; preferably substituted or unsubstituted phenyl; $R_2$ is a straight or branched alkyl having 1 to 12 carbon atoms; and $R_3$ is a straight or branched alkyl having 1 to 12 carbon atoms; starting from a di-keto compound according to Formula B wherein $R_3$ is as shown above, which compound is converted into a ketoenamine compound according to Formula C wherein $R_2$ and $R_3$ are as shown above, which ketoenamine compound is then reduced to an amino alcohol according to Formula D, wherein $R_2$ and $R_3$ are as shown above, that is subsequently converted into a compound according to Formula A: characterized in that the ketoenamine is reduced into an amino alcohol using a nickel aluminium alloy in an aqueous solution of an inorganic base.

According to the present invention said reduction of compound C into compound D is carried out by using a nickel-aluminium alloy in an aqueous alkaline solution. This has the effect of replacing sodium metal in an isopropanol-tetrahydrofuran solvent, which is beneficial since the handling of a nickel-aluminium alloy is comparatively more safe than sodium metal, especially on a plant scale. Moreover, an aqueous solution can be used for the reduction reactions therewith reducing the need of organic solvents such as isopropanol and tetrahydrofuran.

After the reduction from compound C to compound D there are at least two possible routes to obtain an compound according to Formula A. A first route being the direct formation of compound A from compound D, which is the first aspect of the invention. A second route being the formation of compound E from compound D and then the formation of compound A from compound E. This is the second aspect of the present invention. The first aspect has as one of its advantages that it is a quick, easy and cheap process including as few process steps as possible. The second aspect has as one of its advantages that more different compounds may be prepared, being a compound wherein two $R_1$ groups (on the carbonate and the carbamate moiety) differ from each other.

In a first aspect, the present invention relates to a process comprising the following steps:

step A1) converting a di-keto compound according to Formula B into a ketoenamine compound according to Formula C;

step A2) reduction of the ketoenamine compound according to Formula C obtained in step A1) to form an amino alcohol compound according to Formula D, said reduction being carried out using a nickel aluminium alloy in an aqueous solution of an inorganic base;

step B) reacting the amino alcohol compound according to formula D obtained in step A2) with an aryloxy halide compound $R_1$—C(=O)X, wherein X is a halide, preferably Cl, using pyridine or sodium hydride in a solvent to prepare the compound according to Formula A.

According to this first aspect, the amino alcohol compound is reacted in one single step (preferably in situ) to AB by an aryloxy halide compound in with pyridine (or sodium hydride) as a base.

In a second aspect, the present invention relates to a process comprising the following steps:

step A1) converting a di-keto compound according to Formula B into a ketoenamine compound according to Formula C;

step A2) reduction of the ketoenamine compound according to Formula C obtained in step A1) to form an amino alcohol compound according to Formula D, said reduction being carried out using a nickel aluminium alloy in an aqueous solution of an inorganic base;

step A3) reacting the amino alcohol compound according to formula D obtained in step A2) with an aryloxy halide compound according to the Formula $R_1$—C(=O)X, wherein X is a halide, preferably Cl, and wherein $R_1$ is the same as cited above in an aqueous solution of an inorganic base to give a amide alcohol compound according to Formula E;

step B') reacting the amide alcohol compound according to Formula E obtained in step A) with an aryloxy halide compound $R_1$—C(=O)X, wherein X is a halide, preferably Cl, using sodium hydride (pyridine may also be used instead of sodium hydroxide but is not preferred) in a solvent to prepare the compound according to Formula A. When pyridine is used, an additional purification step is required.

According to this second aspect, the amino alcohol compound is reacted in two subsequent steps (preferably in one single pot) to AB by an aryloxy halide compound, first in an aqueous solution of an inorganic base (in which the $R_1$ group is added to the carbamate moiety) and secondly using sodium hydride or pyridine (in which the $R_1$ group is added to the carbonate moiety). According to this aspect, preferably no pyridine is required which decreases the pollution and for some application, such as healthcare, it is required that no pyridine is present. According to this embodiment, the amino alcohol was first converted to a monobenzoate, being a new intermediate not known in the previous synthesis of AB; this compound is preferably purified and isolated prior to step B'). This aspect provides an increase in yield from 54% to 64% (lab scale) as well as a reduction in overall reaction time from 45 hours to 29 hours.

List of Definitions

The following definitions are used in the present description and claims to define the stated subject matter. Other terms not cited below are meant to have the generally accepted meaning in the field.

"Ziegler-Natta catalyst" as used in the present description means: a transition metal-containing solid catalyst compound comprises catalytic species (viz. a transition metal-containing species comprises a transition metal halide selected from titanium halide, chromium halide, hafnium halide, zirconium halide and vanadium halide) supported on a metal or metalloid compound (e.g. a magnesium compound or a silica compound).

"internal electron donor" as used in the present description means: an electron-donating compound containing one or more atoms of oxygen (O) and/or nitrogen (N).

"halide" as used in the present description means: an ion selected from the group of: fluoride (F—), chloride (Cl—), bromide (Br—) or iodide (I—).

"alkyl" as used in the present description means: an alkyl group being a functional group or side-chain consisting of carbon and hydrogen atoms having only single bonds. An alkyl group may be straight or branched and may be un-substituted or substituted.

"having 6 to 20 carbons" as used in the present description means: a group having 6, 7, 8, 9, 10, 11, 12, 13, 14, 15, 16, 17, 18 19, or 20 carbon atoms.

"having 1 to 12 carbons" as used in the present description means: a group having 1, 2, 3, 4, 5, 6, 7, 8, 9, 10, 11, or 12 carbon atoms.

Unless stated otherwise, when it is stated that any R group is "independently selected from" this means that when several of the same R groups are present in a molecule they may have the same meaning or they may not have the same meaning.

The present invention is described below in more detail. All embodiments described with respect to one aspect of the present invention are also applicable to the other aspects of the invention, unless otherwise stated.

DETAILED DESCRIPTION AND DESCRIPTION OF EMBODIMENTS

The present invention is related to a process for the synthesis according to claim 1, starting with a di-keto compound that is first converted into a ketoenamine compound (Formula C) that is subsequently reduced to an amino alcohol compound, that is reacted in other one or two steps with an aryloxy halide compound to give a compound according to Formula A.

The advantage of the present invention is that there is no longer need for less safe reducing agents such as sodium metal. In addition, the overall reaction time is reduced and the yield is increased.

Step A1)

In an embodiment, the temperature of reaction during step A1) is between 10 and 30° C., preferably between 15 and 20° C. In an embodiment, step A1) is carried out in an aqueous environment; in other words, the reaction mixture of step A1) is aqueous. In an embodiment, the compound $R_2NH_2$ is added in the form of an aqueous solution. In an embodiment, the molar ratio between the compound according to Formula B and the compound $R_2NH_2$ during step A1) is between 1.0:2.0 and 2.0:1.0, preferably between 1.0:1.5 and 1.5:1.0, more preferably between 1.0:1.2 and 1.2:1.0. In an embodiment, the reaction time of step A1) is between 30 minutes and 5 hours; preferably between 2 and 3 hours. In an embodiment, the product of step A1) is not isolated prior to step A2). In an embodiment, the reaction mixture obtained in step A1) is used in step A2) without isolation of the ketoenamine compound according to formula C. In an embodiment, water is used as the solvent in step A1). In an embodiment of the present invention or of the first or second aspect of the present invention, ketoenamine may be obtained from acetyl acetone in step A1) according to the procedure as disclosed in EP 1 867 264 B1. In an embodiment of the present invention or of the first or second aspect of the present invention, the obtained ketoenamine in its reaction mixture of step A1)—without any isolation or purification—is used directly is step A2). In other words, ketoenamine is in situ reduced to an amino alcohol. In an embodiment, step A1) of converting a di-keto compound according to Formula B into a ketoenamine compound of Formula C is carried out using an aqueous solution of $R_2$—$NH_2$. In an embodiment, as $R_2$—$NH_2$ methyl amine or ethyl amine is used, wherein $R_2$ is respectively methyl or ethyl.

Step A2)

In an embodiment, the temperature of reaction during step A2) is between 5 and 30° C., preferably between 10 and 20° C. In an embodiment, step A2) is carried out by adding an inorganic base, preferably in the form of an aqueous solution, to the reaction mixture obtained in step A1).

In an embodiment, the nickel-aluminium alloy is added over a period of time of preferably between 1 to 10 hours, such as between 3 and 5 hours.

In an embodiment, the nickel-aluminium alloy is added in the form of a solid, preferably a powder.

In an embodiment, the reaction time after the addition of the alloy is complete is between 5 and 19 hours, preferably between 10 and 12 hours. The total reaction time during step A2) is preferably between 6 and 24 hours, such as between 13 and 19 hours.

In an embodiment, the molar ratio between the compound according to Formula B and the inorganic base during step A2) is between 1.0:2.0 and 1.0:20.0, preferably between 1.0:3.0 and 1.0:10.0, more preferably between 1.0:4.0 and 1.0:7.0. In an embodiment, the molar ratio between the compound according to Formula B and the alloy during step A2) is between 1.0:1.0 and 1.0:5.0, preferably between 1.0:1.5 and 1.0:3.0, more preferably between 1.0:1.75 and 1.0:2.25. In this embodiment, at least a stoichiometric amount of alloy is used or an excess of alloy. In another embodiment, the molar ratio between the compound according to Formula B and the alloy during step A2) is between 20.0 to 1.0 and 5.0 to 1.0, preferably between 20.0 and 1.0 and 6.6 to 1.0, such as 10.0 to 1.0. In this embodiment, between 5 and 20 molar %, such as between 5 and 15 molar %, for example 10 molar % of the alloy is used and in this embodiment hydrogen gas is added to the reaction mixture (e.g. by bubbling) allowing the reaction to go to completion. Without wishing to be bound to a particular theory, the inventor believes that by the reaction of the hydroxide with the nickel aluminium alloy will lead to aluminium salts and the in situ generation of hydrogen that will drive the reaction. In this embodiment, the reaction is started by the alloy acting as a catalyst and the reaction is driven to completion by the addition of additional hydrogen, e.g. by bubbling hydrogen gas through the reaction mixture. This specific embodiment reduces the amount of solid aluminium salt that is added when a stoichiometric or excess of alloy is used.

In an embodiment, the product of step A2) is not isolated prior to step A3). In an embodiment, the reaction mixture obtained in step A2) is used in step A3) without isolation of the amino alcohol compound according to formula D. In an embodiment, the product according to Formula D is isolated prior to step B). In an embodiment, water is used as the solvent in step A2).

In an embodiment, as nickel-aluminium alloy was used an alloy comprising between 30 and 50 wt. % of nickel and between 50 and 70 wt % of aluminium, preferably an alloy comprising 50 wt % Ni and 50 wt % Al or 30 wt % Ni and 70 wt % Al.

In an embodiment, the product is obtained in the form of an oil.

In an embodiment, said inorganic base in said aqueous solution (forming an aqueous basic solution) used in step A2) is a an alkali hydroxide, preferably sodium hydroxide or potassium hydroxide.

In an embodiment, step A2) is carried out directly after step A1) without isolating of the ketoenamine compound of formula C that is formed in step A1).

In an embodiment, the nickel aluminium alloy used in step A2) is separated as a solid from the liquid reaction mixture obtained after step A2) and wherein the liquid reaction mixture comprising the aqueous solution of an inorganic base is used as the aqueous solution in step A3).

In an embodiment, the reaction mixture of step A2) is filtrated providing a retentate comprising the nickel aluminium alloy and wherein the filtrate comprising the aqueous solution of an inorganic base and the amino alcohol of Formula D is used as the starting material of step A3).

In an embodiment, said aqueous alkaline solution used in step A2) and/or in step A3) is a solution of sodium hydroxide and/or potassium hydroxide in water.

Step A3)

In an embodiment, the temperature of reaction during step A3) is between 5 and 30° C., preferably between 10 and 15° C. In an embodiment, step A3) is carried out by adding an aryloxy halide to the reaction mixture obtained in step A2).

In an embodiment, the reaction time is between 10 minutes and 2 hours, preferably between 45 and 90 minutes.

In an embodiment, the molar ratio between the compound according to Formula D and the aryloxy halide during step A3) is between 1.0:50.0 and 1.0:200.0, preferably between 1.0:100.0 and 1.0:140.0.

In an embodiment, the product of step A3) is isolated prior to step B').

In an embodiment, water is used as the solvent in step A3).

In an embodiment, the product is obtained in the form of an oil.

In an embodiment, as aryloxy halide compound $R_1$—C(=O)X benzoyl chloride is used, wherein $R_1$ is phenyl and wherein X is chloride. In an embodiment, the aryloxy halide used in step A3) is the same as the aryloxy halide in step B').

In an embodiment, said aqueous alkaline solution used in step A2) and/or in step A3) is a solution of sodium hydroxide and/or potassium hydroxide in water.

Step B)

In an embodiment, step B) is carried out in a solvent, preferably toluene.

In an embodiment, the temperature during step B) is between 15 and 40° C., preferably between 25 and 30° C.

In an embodiment, the molar ratio between the compound according to formula D and pyridine is between 1.0:1.0 and 1.0:5.0, preferably between 1.0:2.0 and 1.0:4.0, preferably between 1.0:2.5 and 1.0:3.5.

In an embodiment, the reaction time of step B) is between 30 minutes and 5 hours, such as between 45 and 90 minutes.

In an embodiment, the solvent is selected from the group consisting of toluene, xylene, ethyl benzene and mono chlorobenzene.

In an embodiment, the invention relates to a process for the synthesis of a compound according to the Fisher projection of Formula A.

Step B')

In an embodiment, step B') is carried without a solvent. In an embodiment, the solvent is selected from the group consisting of toluene, xylene, ethyl benzene and mono chlorobenzene.

In an embodiment, the temperature during step B') is between 60 and 100° C., preferably between 70 and 90° C.

In an embodiment, the molar ratio between the compound according to formula E and sodium hydroxide (or pyridine) is between 1.0:1.0 and 1.0:3.0, preferably between 1.0:1.2 and 1.0:1.7, preferably between 1.0:1.4 and 1.0:1.6.

In an embodiment, the reaction time of step B) is between 10 and 50 minutes, such as between 20 and 40 minutes.

In an embodiment, the invention relates to a process for the synthesis of a compound according to the Fisher projection of Formula A.

In an embodiment, as a diketo compound according to Formula B acetyl acetone is used, wherein $R_3$ is methyl or wherein as a diketo compound according to Formula B 2,2,6,6-tetramethyl-3,5-heptandion (dipivaloylmethane) is used, wherein $R_3$ is tert-butyl.

In the claims, the word "comprising" does not exclude other elements or steps, and the indefinite article "a" or "an" does not exclude a plurality. The scope of the present invention is defined by the appended claims. One or more of the objects of the invention are achieved by the appended claims.

EXAMPLES

The present invention is further elucidated based on the Examples below which are illustrative only and not considered limiting to the present invention.

Example 1 According to the First Aspect of the Invention

Step A1) Converting a Di-Keto Compound into a Ketoenamine

Acetyl acetone (100 g, 1.0 mole) was charged into a round bottom flask and cooled to a temperature of between 15 and 20° C. To this, an aqueous methylamine ($R_2NH_2$, wherein $R_2$=Me) solution (85.25 g, 1.1 moles) was slowly added while the temperature of the reaction mixtures was between kept between 15 and 20° C. The reaction mixture was stirred for a period of between 2 and 3 hours at the same temperature to give the ketoenamine. This product was however not isolated and the reaction was directly proceeded with step A2).

Step A2) Reduction of Ketoenamine to an Amino Alcohol

To the reaction mixture of step A1) was added an aqueous sodium hydroxide solution (215 g NaOH in 850 ml water, 5.35 mole with respect to acetyl acetone). The mixture was cooled to a temperature of between 10 and 20° C. To this mixture, a nickel-aluminium alloy (50 wt. %/50 wt. %) powder (170 g, 1.98 mole) was slowly added over the course of a period of 3 to 5 hours until an effervesce of hydrogen gas was observed. After this addition of the nickel-alloy powder, the reaction mixture was stirred for an additional period of 10 to 12 hours. After the reaction was completed, the reaction mixture was filtered. The solids obtained were washed with 100 ml of water. The filtrate consists of two layers: the aqueous layer was discarded and the organic layer containing the product was washed with 120 g of an aqueous 50% NaOH solution for a period of between 15 and 20 minutes at room temperature (23° C.). The resulting two layers were separated: the aqueous layer was discarded and the organic layer was washed once again with 120 g of an aqueous 50% NaOH solution for a period of between 15 and 20 minutes at room temperature. The resulting two layers were separated: the aqueous layer was discarded and the organic layer was checked for its moisture level which was (and should be) below 1%. A product was obtained in an amount of 115 gram, having a purity of 99% (isomer mix) according to Gas chromatography and having an moisture content of 1.14%.

Step B) Reacting the Amino Alcohol with an Aryloxy Halide Compound to Give Compound A The following compounds: 4-(methyl amino) pentan-2-ol (30 g, 0.256 mole), 120 ml toluene and pyridine (62 ml, 60 g, 0.768 mole) were charged into a round bottom flask and brought to a temperature of between 25 and 30° C. To this mixture was slowly added (90.0 g, 0.640 mole) benzoyl chloride. the temperature of the reaction mixture being between 25 and 50° C. The reaction mixture was then stirred for 1 hour at the same temperature. Then the resulting suspension was heated to a temperature of between 60 and 70° C. and was maintained at that temperature for a period of between 4 and 6 hours. After the reaction was completed, the reaction mass was cooled to room temperature and washed with water. The biphasic system was separated into a lower aqueous layer and an upper organic layer. The aqueous layer was discarded and the organic layer was washed with an aqueous 5% NaOH solution to remove benzoic acid and benzoic anhydride (if any). The resulting two layers where separated and the aqueous layer was discarded, the organic layer was stirred with water for a period of between 15 to 20 minutes at room temperature (23° C.). The resulting two layers where separated and the aqueous layer was discarded, the organic layer was evaporated removing the solvents using a rotary evaporator at 2 mbar vacuum and at a temperature of between 60 and 95° C. resulting in 75.0 g (92% yield) of solid 4-(methyl amino) pentan-2-ol dibenzoate having a purity of >95% (isomer mix) as determined by gas chromatography. The overall yield is 88% based on acetyl acetone.

Example 2 According to the First Aspect of the Invention

Step A1) Converting a Di-Keto Compound into a Ketoenamine

Acetyl acetone (50 g, 0.5 mole) was charged into a round bottom flask and cooled to a temperature of between 15 and 20° C. To this, an aqueous methylamine 40% solution (42.6 g, 0.55 moles) was slowly added while the temperature of the reaction mixtures was between kept between 15 and 20° C. The reaction mixture was stirred for a period of between 2 and 3 hours at the same temperature. To give the ketoenamine. This product was however not isolated and the reaction was directly proceeded with step A2).

Step A2) Reduction of Ketoenamine to an Amino Alcohol

To the reaction mixture of step A1) was added an aqueous sodium hydroxide solution (30 g NaOH in 400 ml water, 5.0 mole with respect to acetyl acetone). The mixture was cooled to a temperature of between 10-20° C. To this mixture, a nickel-aluminium alloy (50 wt. %/50 wt. %) powder (30.0 g, 0.35 mole) was slowly added in small lots to avoid frothing. After this addition of the nickel-alloy powder, bubble hydrogen gas at normal pressure and room temperature for 3-5 hours to complete the reduction. After the reaction was completed, the reaction mixture was filtered. The solids obtained were washed with 50 ml of water. To the filtrate 70 gm NaOH was added slowly under stirring and stirred for 30 min. The above organic layer containing the product was separated and 10 g NaOH was added to the oil to separate water. The resulting two layers were separated: the aqueous layer was discarded and the organic layer was checked for its moisture level which was (and should be) below 1%. A product was obtained in an amount of 52 gram (yield of 88%), having a purity of 99% (isomer mix) according to Gas chromatography and having an moisture content of 1.2%.

Example 3 According to the Second Aspect of the Invention

Step A1) Converting a Di-Keto Compound into a Ketoenamine

To a 1 L four neck round bottom flask, equipped with a water condenser, 40% monomethyl amine ($R_2NH_2$; $R_2$=Me) solution in water (12.2 g, 120 mmol) was charged. Acetyl acetone (10.0 g, 100 mmol) was added drop wise to the above solution at a temperature of between 10 and 15° C. After the addition, the reaction mass was stirred at room temperature (23° C.) for 3 hours. The reaction was monitored by gas chromatography and a ketoenamine was produced in a purity of >99% (determined by gas chromatograph by taking 1 mL reaction mixture, extracting with 1 mL methylene dichloride/toluene and analysing) and was not isolated; the reaction mixture was directly used in step A2.

Step A2) Reduction of Ketoenamine to an Amino Alcohol

To the aqueous solution of ketoenamine obtained in step A1, a cold (10-20° C.) aqueous sodium hydroxide solution (21.4 g, 535 mmol, in 85 mL water) was added. The resulting solution was then cooled to a temperature of between 10 and 20° C. by using an ice-water mixture. To this solution, a nickel-aluminium alloy powder (Ni 50% Al 50%) (17.13 g, 200 mmol) was added slowly in small portions within 3 hours while maintaining the temperature of the reaction mixture at a temperature of between 10 and 20° C. by using an ice water mixture; this exothermic reaction evolves hydrogen gas. After the addition of nickel-aluminium powder, the reaction mass was stirred for 16-18 h (overnight) at room temperature. The reaction was monitored by GC and samples were prepared by taking out 5-10 mg of oil/product from upper layer and diluted by 1 mL methylene dichloride/toluene for GC analysis. After the completion of reaction—as determined by GC, the reaction mass was filtered and the resulting cake was washed with 4×10 mL of water. Note: this reduction generates hydrogen and should be performed in an efficient hood. The nickel that is removed by filtration is potentially pyrophoric and should not be sucked dry for extended periods. It should be allowed to dry in metal trays in the absence of flammables for a period of 24 hours before disposal. The filtrate comprised an alkaline solution and the amino alcohol according to Formula C which was not isolated but directly used in the following step, step A3.

Step A3) Reacting the Amino Alcohol with an Aryloxy Halide Compound to Give a Amide Alcohol To the aqueous filtrate obtained in step A2) was added benzoyl chloride (16.86 g, 120 mmol) at a temperature of between 10 and 15° C. and the solution was stirred for an hour at 10 to 15° C. after the addition was completed. The reaction was monitored by GC and samples were prepared by extracting 1 mL of reaction mass with 1 mL methylene dichloride/toluene for GC analysis. The product, monobenzoate was isolated by separating it in the form of oil by means of a separating funnel. The product was extracted in toluene (2×50 mL). The organic layer was evaporated on a rotary evaporator under reduced atmospheric pressure. Crude weight of monobenzoate was 19.70 g (oil with 89% yield and 85.8% purity by GC along with 6% AB and other minor impurities).

Subsequently, the monobenzoate was purified as follows. The crude monobenzoate was distilled for removal of lower volatiles and one fraction was collected at outer bath temperature: 155-160° C.; vapour temperature: 60-75° C. and Pressure: 10-3 mbar. The monobenzoate was obtained as a residual liquid. (17.92 g, 81% Yield, 92.4% Mono AB+5.5% AB by GC). For characterization purpose, monobenzoate was collected as second fraction with 93.8% GC purity as an isomeric mixture at retention time 16.75 and 17.04 min. Calculated m/z: 221.4 (100.0%), 222.14 (14.1%). Observed m/z in GCMS: 221.13. FT-IR analysis showed presence of free —OH group of an alcohol, which absorbs at higher wavenumber 3391 cm$^{-1}$, C—N stretching at 2967 and 2931 cm$^{-1}$ and carbonyl group of amide at 1600-1610 cm$^{-1}$. The absence of absorbance peaks between 1735-1740 cm$^{-1}$ reveals the absence of ester carbonyl in the compound. $^1$H NMR (300 MHz, dmso-d6) ppm: 0.89-1.17 (m, 6H), 1.65 (m, 2H), 2.69-2.81 (m, 3H), 3.42 (m, 1H), 4.28-4.30 (m, 1H), 7.35-7.85 (m, 5H). —OH proton is not detected. $^{13}$C-NMR (75 MHz, dmso-d6) ppm: 17.74, 18.41, 18.65, 19.31, 24.19, 24.28, 24.73, 26.36, 26.70, 31.33, 31.68, 40.27, 40.54, 40.82, 42.79, 42.99, 43.14, 46.01, 46.43, 51.13, 51.45, 63.28, 63.61, 63.77, 64.10, 78.86, 126.77, 126.84, 127.02, 127.25, 127.49, 128.50, 128.73, 128.76, 129.14, 129.41, 129.50, 129.75, 131.46, 134.99, 137.73, 137.98, 167.05, 170.42, 170.80, 171.18, 171.57. The $^{13}$C-NMR shows four peaks of carbonyl and four peaks of C—O. It revels the presence of four enantiomers in the compound.

Step B') Reacting the Amide Alcohol with an Aryloxy Halide Compound

To a 250 mL round bottom three neck flask, was added 60% sodium hydride (1.35 g, 33.8 mmol) and washed by 2×25 mL hexane under inert atmosphere. The hexane was removed by decantation. To this flask, an azeotropically-dried solution of monobenzoate obtained in step A) (5.0 g, 22.5 mmol) in 75 mL toluene was added. The slurry was heated slowly to a temperature of between 70 and 80° C. and stirred for 0.5 hour. This is exothermic reaction, which involves evolution of hydrogen gas. To this reaction mass, a solution of benzoyl chloride (3.17 g, 24 mmol) in 25 mL, toluene was added slowly, dropwise at 80-90° C. This is exothermic reaction. After 5 minutes of stirring, the reaction mixture was quenched by water. The organic layer was extracted in toluene and dried over sodium sulphate and evaporated on rotary evaporator under reduced atmospheric pressure. As a product 6.0 g of AB was obtained with 81.7% yield and 96.6% purity according to GC. $^1$H NMR (dmso-d6) ppm: 7.95-7.91 (m, 1H), 7.66-7.60 (m, 2H), 7.40-7.03 (m, 5H), 6.78-6.76 (m, 2H), 4.74-5.06 (br m, 1H), 3.91-3.82 (m, 1H), 2.83-2.56 (ddd, 3H), 2.02-1.51 (m, 1H), 1.34-1.25 (dd, 1H), 1.13-1.02 (m. 6H). The overall yield is 66%.

The invention claimed is:

1. Process for synthesis of a compound according to Formula A:

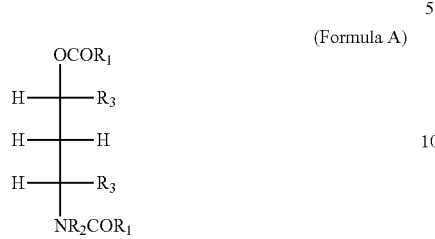
(Formula A)

wherein $R_1$ is a substituted or unsubstituted aryl having 6 to 20 carbon atoms; $R_2$ is a straight or branched alkyl having 1 to 12 carbon atoms; and $R_3$ is a straight or branched alkyl having 1 to 12 carbon atoms; starting from a di-keto compound according to Formula B wherein $R_3$ is as shown above, which compound is converted into a ketoenamine compound according to Formula C wherein $R_2$ and $R_3$ are as shown above, which ketoenamine compound is then reduced to an amino alcohol according to Formula D, wherein $R_2$ and $R_3$ are as shown above, that is converted into a compound according to Formula A:

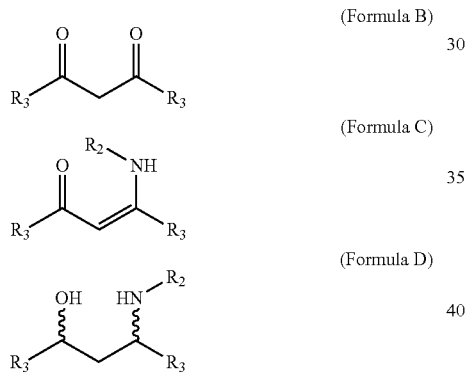
(Formula B)
(Formula C)
(Formula D)

characterized in that the ketoenamine is reduced into an amino alcohol using a nickel aluminium alloy in an aqueous solution of an inorganic base.

2. The process according to claim 1, wherein said process comprises the following steps:

step A1) converting a di-keto compound according to Formula B into a ketoenamine compound according to Formula C:

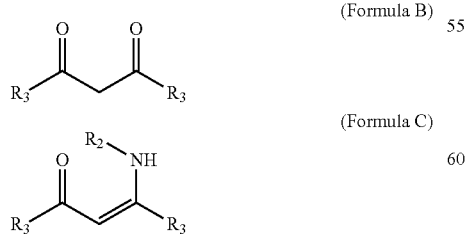
(Formula B)
(Formula C)

step A2) reduction of the ketoenamine compound according to Formula C obtained in step A1) to form an amino alcohol compound according to Formula D, said reduction being carried out using a nickel aluminium alloy in an aqueous solution of an inorganic base:

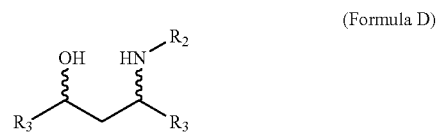
(Formula D)

step B) reacting the amino alcohol compound according to formula D obtained in step A2) with an aryloxy halide compound $R_1$—C(═O)X, wherein X is a halide, using pyridine or sodium hydride in a solvent to prepare the compound according to Formula A.

3. The process according to claim 1, wherein said process comprises the following steps:

step A1) converting a di-keto compound according to Formula B into a ketoenamine compound according to Formula C:

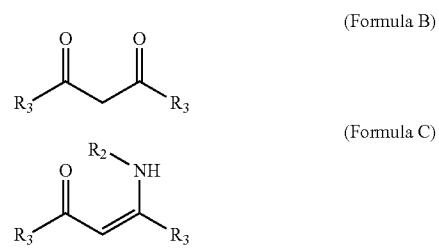
(Formula B)
(Formula C)

step A2) reduction of the ketoenamine compound according to Formula C obtained in step A1) to form an amino alcohol compound according to Formula D, said reduction being carried out using a nickel aluminium alloy in an aqueous solution of an inorganic base:

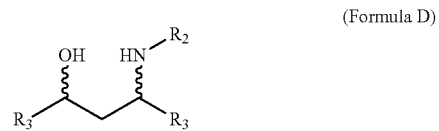
(Formula D)

step A3) reacting the amino alcohol compound according to formula D obtained in step A2) with an aryloxy halide compound according to the Formula $R_1$—C(═O)X, wherein X is a halide, and wherein $R_1$ is the same as cited above in an aqueous solution of an inorganic base to give a amide alcohol compound according to Formula E;

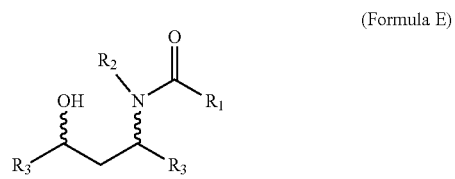
(Formula E)

step B') reacting the amide alcohol compound according to Formula E obtained in step A) with an aryloxy halide compound $R_1$—C(═O)X, wherein X is a halide, using sodium hydride or pyridine, in a solvent to prepare the compound according to Formula A.

4. Process according to claim 2, wherein step A1) of converting a di-keto compound according to Formula B into a ketoenamine compound of Formula C is carried out using an aqueous solution of $R_2$—$NH_2$.

5. Process according to claim 2, wherein step A2) is carried out directly after step A1) without isolating of the ketoenamine compound of formula C that is formed in step A1).

6. Process according to claim 3, wherein the nickel aluminium alloy used in step A2) is separated as a solid from the liquid reaction mixture obtained after step A2) and wherein the liquid reaction mixture comprising the aqueous solution of an inorganic base is used as the aqueous solution in step A3).

7. Process according to claim 6, wherein the reaction mixture of step A2) is filtrated providing a retentate comprising the nickel aluminium alloy and wherein the filtrate comprising the aqueous solution of an inorganic base and the amino alcohol of Formula D is used as the starting material of step A3).

8. Process according to claim 2, wherein as aryloxy halide compound $R_1$—C(=O)X benzoyl chloride is used, wherein $R_1$ is phenyl and wherein X is chloride.

9. Process according to claim 3, wherein the aryloxy halide used in step A3) is the same as the aryloxy halide in step B').

10. Process according to claim 1, wherein in step B) or B') the solvent is selected from the group consisting of toluene, xylene, ethyl benzene and mono chlorobenzene.

11. Process according to claim 1, wherein as a diketo compound according to Formula B acetyl acetone is used, wherein $R_3$ is methyl or wherein as a diketo compound according to Formula B 2,2,6,6-tetramethyl-3,5-heptandion (dipivaloylmethane) is used, wherein $R_3$ is tert-butyl.

12. Process according to claim 4, wherein as $R_2$—$NH_2$ methyl amine or ethyl amine is used, wherein $R_2$ is respectively methyl or ethyl.

13. Process according to claim 2, wherein said aqueous alkaline solution used in step A2) and/or in step A3) is a solution of sodium hydroxide and/or potassium hydroxide in water.

* * * * *